United States Patent [19]

Coates

[11] 4,219,019
[45] Aug. 26, 1980

[54] BANDAGE

[75] Inventor: John T. Coates, Hoffman Estates, Ill.

[73] Assignee: The Kendall Company, Boston, Mass.

[21] Appl. No.: 10,102

[22] Filed: Feb. 7, 1979

[51] Int. Cl.³ .............................................. A61L 15/00
[52] U.S. Cl. ................................................... 128/156
[58] Field of Search ................................ 128/155–156, 128/284, 287, 290 R, 290 W, 296

[56] References Cited

U.S. PATENT DOCUMENTS

| | | | |
|---|---|---|---|
| 3,067,747 | 12/1962 | Wolterding et al. | 128/296 |
| 3,542,634 | 11/1970 | Such et al. | 128/156 |
| 3,545,442 | 12/1970 | Wicker et al. | 128/156 |
| 3,927,669 | 12/1975 | Glatt | 128/156 |

Primary Examiner—C. Fred Rosenbaum
Attorney, Agent, or Firm—Powell L. Sprunger

[57] ABSTRACT

A bandage comprising, a tape strip having a pressure-sensitive adhesive on a front surface thereof to secure the bandage on a patient. The bandage has an absorbent pad comprising a sheet of nonwoven fabric secured on the front surface of the tape strip. The sheet has an inner layer of substantially hydrophilic fibers, and an outwardly facing surface layer of substantially hydrophobic fibers. The inner and surface layers are bonded together in substantially isolated highly compacted areas defining adjacent regions of substantially less compaction. The fabric is formed in a repeating series of wave-like undulations substantially throughout the dimensions of the fabric, with the interfiber spaces in the areas being substantially closed, and with the interfiber spaces in the regions being substantially open.

10 Claims, 9 Drawing Figures

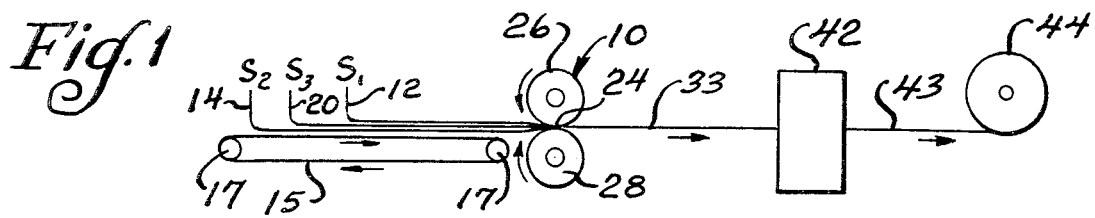
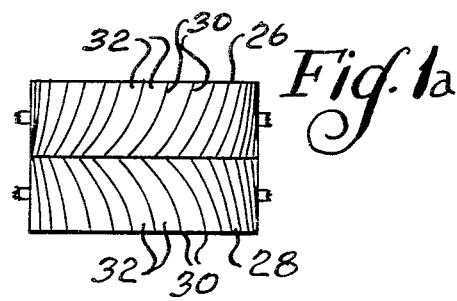
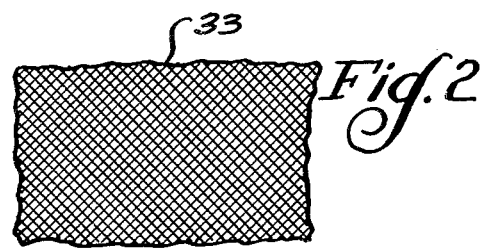
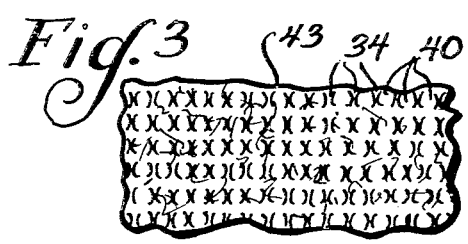
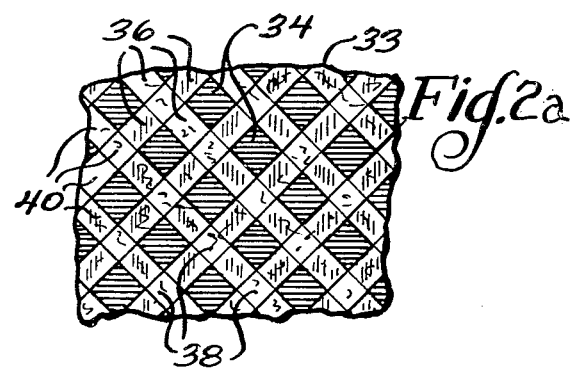
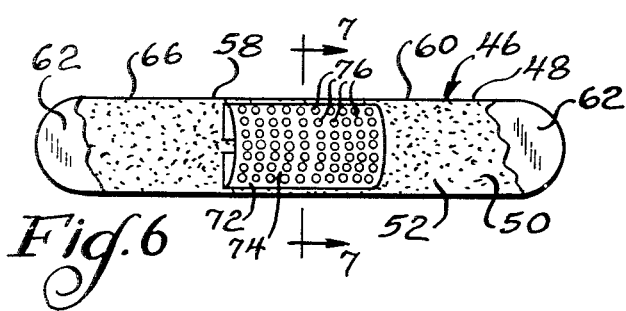
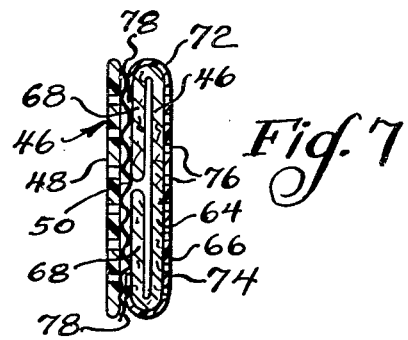
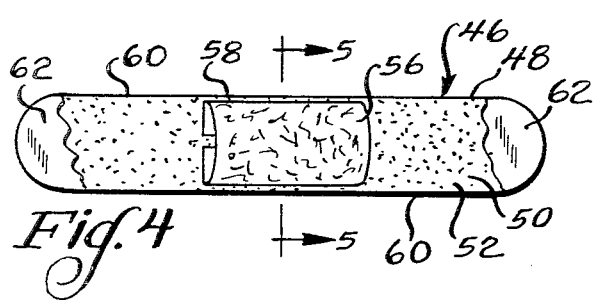
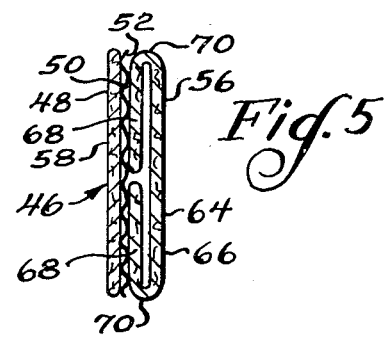

BANDAGE

BACKGROUND OF THE INVENTION

The present invention relates to absorbent articles, and more particularly to bandages.

A various assortment of bandages have been proposed in the past for use on patients. Typically, such bandages have an absorbent pad secured on a tape strip. However, since such pads are normally adherent to the patient's wound, the bandages have required the use of an additional plastic sheet having apertures to cover the pad and prevent this result. Unfortunately, the covering sheet is semi-occlusive and non-absorbent, and may deter the desired transfer of body fluids from the wound into the pad. Further, the cover sheets detract from the cushioning and surface characteristics desired for the wound.

SUMMARY OF THE INVENTION

A principal feature of the present invention is the provision of an improved bandage of simplified construction.

The bandage of the present invention comprises, a tape strip having a pressure-sensitive adhesive on a front surface thereof to secure the bandage on the patient. The bandage has an absorbent pad comprising a sheet of nonwoven fabric secured on the front surface of the tape strip. The sheet has an inner layer of substantially hydrophilic textile length fibers, and first and second surface layers of heat-sensitive substantially hydrophobic textile length fibers on opposed sides of the inner layer. The inner and outer surface layers are fused together in relatively small bonding areas defining adjacent unbonded regions of the fibers isolating the areas from each other. The fabric is formed in a repeating series of wave-like undulations substantially throughout the fabric.

A feature of the present invention is that the interfiber spaces in the fused areas are substantially closed to prevent tissue ingrowth and render the areas nonadherent to the wound.

A further feature of the present invention is that the outer layer provides a predominantly hydrophobic surface for contacting the wound and render the regions nonadherent to the wound.

Thus, a feature of the invention is that the pad itself is substantially nonadherent to the wound, and eliminates the need for a separate plastic cover sheet.

Still another feature of the invention is that the interfiber spaces of the regions are substantially open to provide the pad with an improved absorbent capacity.

Yet another feature of the invention is that the inner layer of hydrophilic fibers enhances the fluid transfer rate from the wound through the outer hydrophobic fibers into the pad.

Thus, a feature of the present invention is that the pad itself has excellent absorbency characteristics while being nonadherent to the wound.

A further feature of the invention is that the pad has a considerable amount of bulk and conformability.

Thus, another feature of the invention is that the pad provides a comfortable surface and a cushioning effect for the patient's wound.

Further features will become more fully apparent in the following description of the embodiments of this invention and from the appended claims.

DESCRIPTION OF THE DRAWINGS

In the drawings:

FIG. 1 is a diagrammatic view illustrating an apparatus for constructing the pad material in a bandage of the present invention;

FIG. 1a is a diagrammatic view illustrating a pair of rolls in the apparatus of FIG. 1;

FIG. 2 is a fragmentary plan view illustrating a nonwoven fabric constructed by the apparatus of FIG. 1 in a stage prior to completion;

FIG. 2a is a fragmentary plan view of the fabric of FIG. 2 taken on an enlarged scale;

FIG. 3 is a fragmentary plan view of the completed fabric constructed by the apparatus of FIG. 1;

FIG. 4 is a front plan view of a bandage of the present invention;

FIG. 5 is a sectional view taken substantially as indicated along the line 5—5 of FIG. 4;

FIg. 6 is a front plan view of another embodiment of a bandage of the present invention; and FIG. 7 is a sectional view taken substantially as indicated along the line 7—7 of FIG. 6.

DESCRIPTION OF THE PREFERRED EMBODIMENTS

Referring now to FIGS. 1 and 1a, there is shown in diagrammatic form an apparatus generally designated 10 for constructing a nonwoven fabric or pad material for use in a bandage of the present invention. The apparatus 10 may have suitable sources $S_1$ and $S_2$ which supply first and second outer or surface layers 12 and 14 of a heat-sensitive fibrous hydrophobic material to an endless belt 15 which is supported and driven by a pair of spaced rolls 17 in a direction as indicated by the arrows in the drawing. The layers 12 and 14 may be constructed from any suitable heat-sensitive hydrophobic fiber such as polypropylene or nylon, and, in a preferred form, the layers 12 and 14 comprise textile-length polyester fibers. Also, if desired, the surface of the fibers in layers 12 and 14 may be treated with a wetting agent to render them more hydrophilic, thus improving the fluid transfer rate and absorbent capacity of the constructed bandage pad without impairing the nonadherence of the pad for a patient's wound. A suitable polyester fiber for use in the layers 12 and 14 having a solid hydrophilic finish is sold by Eastman Kodak Company, Rochester, New York, under the fiber product No. 432. The apparatus 10 also has a source $S_3$ of substantially hydrophilic fibers, such as a blend of hydrophobic fibers and predominant hydrophilic fibers, which is supplied to the belt 15 in the form of an inner or central layer 20 intermediate the outer layers 12 and 14. In a preferred form, the inner layer 20 comprises a blend or mixture of textile-length rayon fibers and textile-length polyester binder fibers, and the polyester fibers may be provided with a hydrophilic finish, as previously discussed in connection with the outer layers 12 and 14, if desired. In a suitable form, the inner layer 20 may comprise rayon fibers in a range of 20 to 99% by weight and polyester fibers in a corresponding range of 80 to 1% by weight, and a preferred range of 75% to 85% rayon fibers and 25% to 15% polyester fibers by weight. In a preferred form, the polyester binder fibers in the central layer 20 soften at a temperature lower than the fibers in the layers 12 and 14, and may comprise a 3.0 denier, 1½ inch polyester fiber, Type 450, sold by Celanese Fibers Marketing Company, New York, New York. Each of the outer layers 12 and 14 may have a weight approximating 20% of the total fabric weight, while the inner layer may have a weight approximating the remaining 60% of the fabric. Typically, for a fabric having a weight of 30 g./sq. yd. each of the outer layers 12 and 14 has a weight of 6 g./sq. yd. while the inner layer has a weight of 18 g./sq. yd.

As shown, the belt 15 passes the overlying layers 12, 20, and 14 to the nip 24 of a pair of opposed heated rolls 26 and 28 which are rotatably driven by suitable means in a direction as indicated by the arrows in the drawing. With reference to FIG. 1a, the layers are fused or bonded together in areas by heat and pressure as the layers pass between the rolls 26 and 28, which are both engraved with a pattern of helical lands 30 and grooves 32, in order to form a series or pattern of pressure areas of various extent in a nonwoven fabric 33. An apparatus disclosed in U.S. Pat. No. 3,507,943, incorporated herein by reference, may be utilized to accomplish this result.

The characteristics of the fiber displacement pattern in the fabric 33 resulting from fusion of the fibers by the rolls 26 and 28 will be discussed in connection with FIGS. 2 and 2a. As shown, the bonded fabric 33 has highly compacted and fused areas 34 at locations defining a plastic film where a land on the roll 26 has traversed a land on the roll 28. The nonwoven fabric 33 also has intermediately compressed areas 36 where a land on one roll has traversed a groove on the other roll. The fabric 33 also has substantially noncompacted areas 38 where a groove on one roll has traversed a groove on the other roll. The areas 34, 36, and 38 are in the form of quadrilaterals with parallel sides, although adjacent sides may not have equal lengths, and hence the areas may be termed rhomboidal. As shown, the combined areas 36 and 38 define relatively noncompacted and unbonded regions 40 which surround and isolate each of the bonded areas 34, with the spaced areas 34 having interfiber spaces substantially closed during fusion by the rolls. While the fabric shown in the drawings has an inner layer located between a pair of outer hydrophobic layers, it will be understood that a single outer layer of hydrophobic fibers may be utilized to define an outer surface of the fabric, if desired.

With reference to FIG. 1, the bonded nonwoven fabric 33 is then passed to a compacting device 42 which microcrepes and bulks the fabric 33 into a micrexed nonwoven fabric 43, after which the fabric 43 may be wound into a suitable roll 44. The device 42 may be of any suitable type, such as an apparatus disclosed in U.S. Pat. No. 3,260,778, incorporated herein by reference. The nonwoven material or fabric 43 on roll 44 may be subsequently unwound and cut into lengths for use in the pads, as will be further discussed below.

With reference to FIG. 3, the micrexing or compacting procedure causes the interfiber spaces in the unbonded regions 40 of the fabric 43 to become substantially open without destroying the structural integrity of the fused areas 34. Thus, the regions 40 have relatively open interfiber spaces for enhanced absorbency in the fabric 43, since absorbency is largely dependent upon the spacing between the fibers. In this regard, the fabric 33 typically has an absorbent capacity approximately six times its own weight, while the absorbent capacity of the fabric 43 typically has an increased absorbent capacity approximately eleven times its own weight after the micrexing operation. In addition, the interfiber spaces in the fused areas 34 remain substantially closed, and the closed areas 34 in combination with the outer layers of hydrophobic fibers provides a nonadherent surface for contacting a patient's wound. In addition, the micrexing operation results in formation of the fabric into a repeating series of wave-like undulations substantially throughout the length of the fabric, with the undulations extending across the width of the fabric. Thus, the fabric assumes a very bulky configuration in order to provide a soft and conformable pad with cushioning characteristics for added comfort to the patient.

The following example is illustrative of a nonwoven fabric which may be utilized according to the present invention:

EXAMPLE

An array of fiber layers comprising a pair of outer or surface layers of 100% 1.5 denier, 1½" polyester fibers, each being approximately 20% of the total fabric weight (gms/sq. yd.), are placed around an inner core layer comprising 85% 1.5 denier 1 9/16" rayon fibers and 15% 3.0 denier, 1½" polyester binder fibers, with the inner layer being approximately 60% of the total fabric weight, and the layers bonded with heat and pressure as previously described in connection with FIGS. 1 and 1a. The layered fabric is then treated with a mechanical compactor, such as disclosed in U.S. Pat. No. 3,260,778, in order to impart a repeating series of wave-like undulations substantially throughout the fabric length and width and to open the interfiber spaces of the nonbonded regions. The resulting fabric weighs approximately 37.6 gms/sq. yd., and has a thickness of 26.0 mils (as measured by the Ames-Mercer gauge), a bulk of 14.7 cm.$^3$/ gm., and an absorbent capacity of approximately 1100%. The comparative figures of the fabric prior to micrexing are as follows: 34 gm/sq. yd., a thickness of 12.5 mils, a bulk of 7.85, and an absorbent capacity of 640%.

A preferred form of a bandage generally designated 46 of the present invention is illustrated in FIGS. 4 and 5. As shown, the bandage 46 has a tape strip 48 having a pressure-sensitive adhesive 50 of suitable type on a front surface 52 of the strip 48. The bandage 46 has an absorbent pad 56 secured on a central portion 58 of the tape strip 48, and the tape strip has a pair of opposed end portions 60 for securing the bandage 46 on the patient with the pad 56 in place over a wound. The bandage 46 may have a pair of release sheets 62 of suitable type releasably attached to and covering the adhesive 50 on the tape strip end portions 60. The release sheets 62 are removed from the strip end portions 60 at the time of use in order to expose the adhesive 50 and permit placement of the bandage on the patient.

The pad 56 is constructed from the micrexed nonwoven material 43 previously described in connection with FIGS. 1–3. Thus, the fabric 43 from the roll 44 of FIG. 1 is cut to length and formed into the pad 56. As shown, the pad 56 has an elongated central portion 64 defining a front surface 66 for facing the patient's wound. The pad 56 also has a pair of side portions 68 extending from the central portion 64 along a pair of fold lines 70 at opposed sides of the central portion 64. As shown, the side portions 68 of the pad 56 are folded into a configuration with the side portions 68 located intermediate the central portion 64 and the tape strip 48, with the side portions 68 being secured to the adhesive 50 on the central portion 58 of the tape strip 48 in order to retain the pad 56 in place.

Thus, in accordance with the present invention, the bandage 46 has an absorbent pad comprising a micrexed layer of the described nonwoven material 43 which has a relatively high absorbent capacity and fluid transfer rate while being nonadherent to a patient's wound. Further, the bandage pad has a high degree of bulk, such that the pad is soft and conformable to provide a comfortable cushioning effect when placed on the patient's wound.

Although, in a preferred form, the pad 56 of the bandage is placed to directly contact the patient's wound, a film may be utilized to cover the pad, if desired. Such a structure is illustrated in FIGS. 6 and 7, in which like reference numerals designate like parts. Thus, the bandage 46 may have an organic film 72 of suitable material, such as polyethylene terephthalate disclosed in U.S. Pat. No. 2,923,298, incorporated herein by reference, which defines a smooth outer surface 74 for contacting the patient's wound. As shown, the film 72 has a plurality of openings 76 extending through the film to permit passage of body fluids through the film into the pad 56. The film 72 covers an outer surface of the pad 56, and has side portions 78 secured to the adhesive 50 on the tape strip 48 at a location beneath the side portions 68 of the pad 56. The pad 56 of FIGS. 6 and 7 may be constructed as previously discussed in connection with FIGS. 4 and 5.

The foregoing detailed description is given for clearness of understanding only, and no unnecessary limitations should be understood therefrom, as modifications will be obvious to those skilled in the art.

I claim:

1. A bandage, comprising:
   a tape strip having a pressure-sensitive adhesive on a front surface thereof to secure the bandage on a patient; and
   a micrexed absorbent pad comprising a sheet of nonwoven fabric secured on said front surface of the tape strip, said sheet having an inner layer of substantially hydrophilic fibers, and an outwardly facing first surface layer of substantially hydrophobic fibers, said inner and surface layers being bonded together in substantially isolated highly compacted areas defining adjacent regions of substantially less compaction, the layers of said fabric being formed by micrexing into a repeating series of wave-like undulations substantially throughout the dimensions of the fabric, with the interfiber spaces in said areas being substantially closed, and with the interfiber spaces in said regions being substantially open.

2. The bandage of claim 1 including a second surface layer of substantially hydrophobic fibers on an opposed side of said inner layer relative to said first surface layer, said second surface layer being bonded in said areas and having open interfiber spaces in said regions.

3. The bandage of claim 1 wherein said inner layer comprises a blend of rayon fibers and polyester binder fibers.

4. The bandage of claim 1 wherein said outer layer comprises polyester fibers.

5. A bandage, comprising:
   a tape strip having a pressure-sensitive adhesive on a front surface thereof to secure the bandage on the patient; and
   a micrexed absorbent pad comprising a sheet of nonwoven fabric secured on said front surface of the tape strip, said sheet having an inner layer of substantially hydrophilic textile-length fibers, and first and second surface layers of heat-sensitive substantially hydrophobic textile-length fibers on opposed sides of said inner layer, said inner and surface layers being fused together in relatively small bonding areas defining adjacent unbonded regions of the fibers isolating said areas from each other, the layers of said fabric being formed by micrexing into a repeating series of wave-like undulations substantially throughout the fabric with the interfiber spaces in said regions being substantially open and with the interfiber spaces in said areas being substantially closed.

6. The bandage of claim 5 wherein said inner layer comprises a blend of rayon fibers and polyester binder fibers, and said first and second surface layers comprise polyester fibers.

7. A bandage, comprising:
   a tape strip having a pressure-sensitive adhesive on a front surface thereof to secure the bandage on a patient; and
   an absorbent pad comprising a sheet of nonwoven fabric secured on said front surface of the tape strip, said sheet having an inner layer of substantially hydrophilic fibers, and an outwardly facing first surface layer of substantially hydrophobic fibers, said inner and surface layers being bonded together in substantially isolated highly compacted areas defining adjacent regions of substantially less compaction, said fabric being formed in a repeating series of wave-like undulations substantially throughout the dimensions of the fabric, with the interfiber spaces in said areas being substantially closed, and with the interfiber spaces in said regions being substantially open, said sheet having a central portion for facing the patient, and a pair of side portions extending from opposed sides of said central portion and folded intermediate said central portion and said tape strip.

8. The bandage of claim 7 wherein said side portions are secured to the adhesive on a central portion of said tape strip.

9. A bandage, comprising:
   a tape strip having a pressure-sensitive adhesive on a front surface thereof to secure the bandage on a patient; and
   an absorbent pad comprising a sheet of nonwoven fabric secured on said front surface of the tape strip, said sheet having an inner layer of substantially hydrophilic fibers, and an outwardly facing first surface layer of substantially hydrophobic fibers, said inner and surface layers being bonded together in substantially isolated highly compacted areas defining adjacent regions of substantially less compaction, said fabric being formed in a repeating series of wave-like undulations substantially throughout the dimensions of the fabric, with the interfiber spaces in said areas being substantially closed, and with the interfiber spaces in said regions being substantially open, said bandage including a smooth organic film covering an outer surface of said pad and having openings extending through the film.

10. A bandage, comprising:
    a tape strip having a pressure-sensitive adhesive on a front surface thereof to secure the bandage on a patient; and an absorbent pad comprising a sheet of nonwoven fabric secured on said front surface of the tape strip, said sheet having an inner layer of substantially hydrophilic fibers, and an outwardly facing first surface layer of substantially hydrophobic fibers, said inner and surface layers being bonded together in substantially isolated highly compacted areas defining adjacent regions of substantially less compaction, said fabric being formed in a repeating series of wave-like undulations substantially throughout the dimensions of the fabric, with the interfiber spaces in said areas being substantially closed, and with the interfiber spaces in said regions being substantially open, said hydrophobic fibers of the surface and inner layers having a hydrophilic finish on surfaces thereof.

* * * * *